United States Patent [19]

Frost

[11] Patent Number: 4,517,977

[45] Date of Patent: May 21, 1985

[54] CO-AXIAL TUBE SURGICAL INFUSION/SUCTION CUTTER TIP

[75] Inventor: Richard B. Frost, Eastwood, Australia

[73] Assignee: Unisearch Limited, Kensington, Australia

[21] Appl. No.: 287,745

[22] Filed: Jul. 24, 1981

[51] Int. Cl.³ .............................................. A61B 17/32
[52] U.S. Cl. ..................................... 128/305; 604/22
[58] Field of Search ............... 128/305, 752, 753, 754, 128/755; 604/22; 30/240

[56] References Cited

U.S. PATENT DOCUMENTS

| | | | |
|---|---|---|---|
| 3,889,657 | 6/1975 | Baumgarten | 604/22 X |
| 3,945,375 | 3/1976 | Banko | 128/305 |
| 4,274,414 | 6/1981 | Johnson et al. | 128/305 |

Primary Examiner—Michael H. Thaler
Attorney, Agent, or Firm—Holman & Stern

[57] ABSTRACT

Surgical instrument for accurately cutting and removing fibrous tissue comprising a first tube (11) having at one end an end wall (12) disposed in a plane substantially normal to the longitudinal axis of the first tube (11), which end wall contains an aperture (13); a second tube (14) coaxial with the first tube (11) and having at one end wall (15) disposed in a plane substantially normal to the longitudinal axis of the second tube (14) which end wall (15) contains an aperture (16) and lies in closed juxtaposition with the end wall (12) of the first tube (11); a mechanism (17) to enable the tubes (11 and 14) to be rotated relative to one another such that the apertures (13 and 16) are moved into and out of register with one another; ducts (19 and 20) to direct a stream of an irrigating liquid to the one end of the tubes (11 and 14); and ducts (21, 37, 36 and 35) to connect the interior of the second tube (14) to a source of suction.

4 Claims, 4 Drawing Figures

CO-AXIAL TUBE SURGICAL INFUSION/SUCTION CUTTER TIP

TECHNICAL FIELD

The present invention relates to a surgical instrument and more particularly to a surgical instrument useful for cutting fibrous tissue during surgical procedures on humans and animals.

BACKGROUND ART

In certain surgical operations it is necessary to cut out and remove fibrous tissue with a high degree of accuracy and from locations which are frequently inaccessible. An example of such an operation is the removal of brain tumors where the tumor needs to be cut out and removed with the minimum possible damage to the surrounding tissue.

There is available on the market a surgical device intended for use in such situations which comprises a first outer tube which is closed at its free end and has an aperture in its side wall a short distance in from the free end of the tube. A second tube is disposed within the first tube and arranged to reciprocate longitudinally along the first tube past the aperture. In this arrangement when the aperture is pressed against an area of tissue some of the tissue will bulge into the interior of the first tube and be severed by the reciprocating second tube. Substantial disadvantages with this arrangement are that, firstly, the tip of the instrument must be pushed past the tissue to be removed to bring the aperture into juxtaposition with the tissue to be removed and, secondly, it is difficult to accurately direct the cutting operation when moving the instrument laterally of its longitudinal axis as is necessary to continue to offer up the aperture to the tissue to be removed.

DISCLOSURE OF THE INVENTION

The present invention consists in a surgical instrument comprising a first tube having at one end an end wall disposed in a plane substantially normal to the longitudinal axis of the first tube which end wall contains an aperture; a second tube disposed within the first tube and having at one end an end wall disposed in a plane substantially normal to the longitudinal axis of the second tube which end wall lies in close juxtaposition with the end wall of the first tube and contains an aperture; means to enable the tubes to be rotated relative to one another such that the apertures in the end walls of the tubes are moved into register and substantially completely out of register with one another; duct means to direct a stream of a liquid to the said one ends of the tubes; and duct means to connect the interior of the second tube to a source of suction.

The first and second tubes are preferably each cylindrical and disposed coaxially. The aperture in each tube may be solely in the end wall of the tube or it may be placed partially in the end wall and partially in the side wall of the tube. It is, however, essential to have at least part of the aperture in the end wall to allow the very tip of the instrument to have an active cutting function.

In order to obtain a good cutting action it is preferred that the edge of each end wall where it abuts its associated aperture be sharpened to form a cutting blade such that tissue entering the apertures when they are in register will be clearly severed from the adjoining tissue. It is also preferred that the end walls of the two tubes be resiliently urged into juxtaposition by spring means or the like as this also assists in providing a good cutting action.

Any suitable motor may be used to cause the relative rotational movement between the tubes. The motor may either form part of the device itself or it may form a separate unit which drives the surgical instrument through a flexible drive or the like. It is preferred that the inner tube be rotated and the outer tube remain stationary however this is not essential to the present invention. In other embodiments of the invention both tubes may be rotated or only the outer tube may rotate. It is also possible to have the direction of relative rotational movement change periodically should this be necessary.

The duct means to direct a stream of liquid to the said one ends of the tubes preferably comprises an annular space between the two tubes. It is however important that the liquid stream, which is preferably an isotonic saline solution, is directed so that the area of tissue to be removed is irrigated before the liquid is sucked up by the suction source acting through the interior of the second tube.

The duct means connecting the suction source to the interior of the inner tube preferably includes a valve to admit air to the duct means, downstream of the inner tube. This valve means can be used to control the effective amount of suction at the tip of the surgical instrument. As the suction pressure draws tissue into the aperture the extent of the suction pressure substantially determines the rate at which tissue is removed by the surgical instrument. The valve means thus enables the effective cutting rate of the instrument to be controlled while it is being used. The valve means preferably comprises a passage opening into a side wall of the instrument such that a user's thumb may be slid over the opening of the passageway to limit the amount of air flowing into the suction line and thereby to control the suction pressure at the tip of the instrument.

BRIEF DESCRIPTION OF THE DRAWINGS

Hereinafter given by way of example only is a preferred embodiment of this invention described with reference to the accompanying drawings in which.

THE BEST MODE OF CARRYING OUT THE INVENTION

Figure 1:
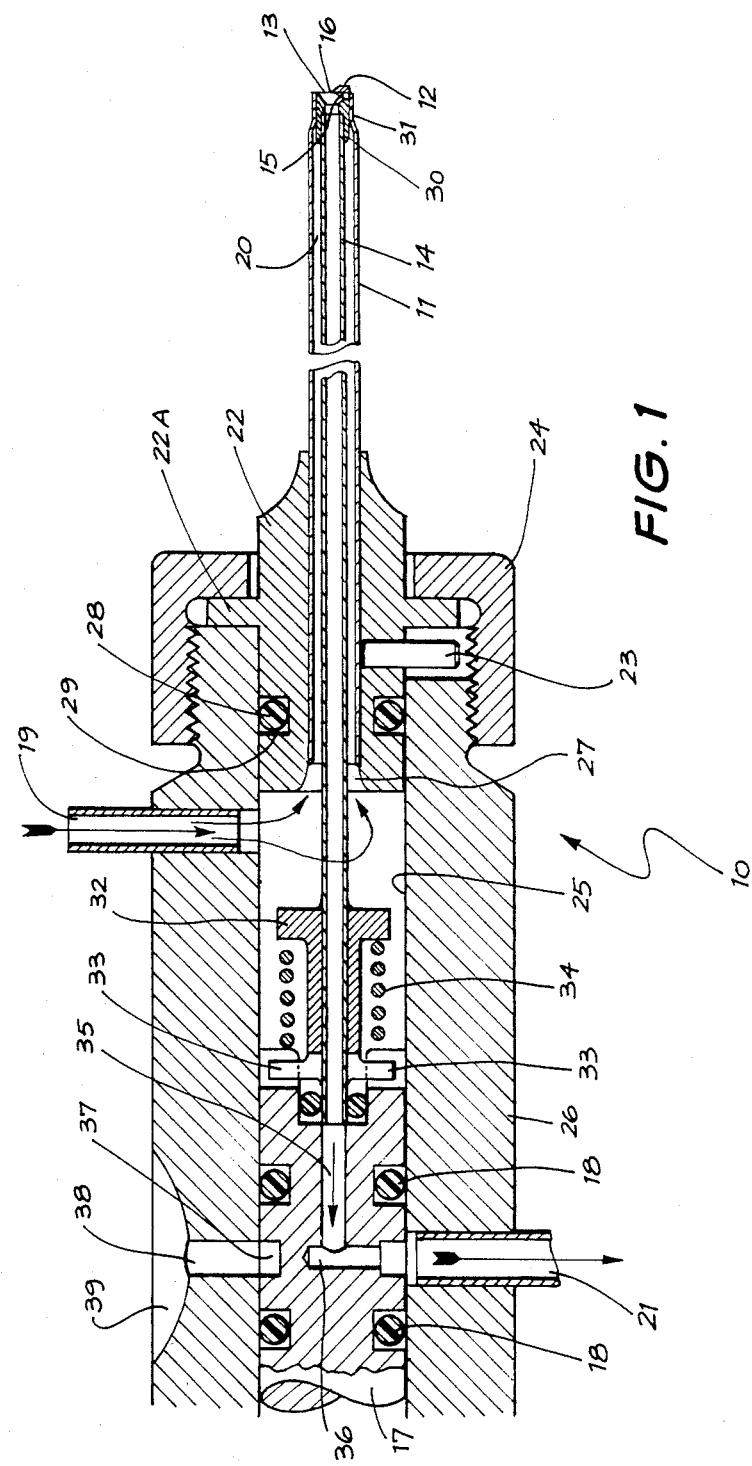
FIG. 1 is a longitudinal sectional view through a surgical instrument according to this invention.
Figure 3:
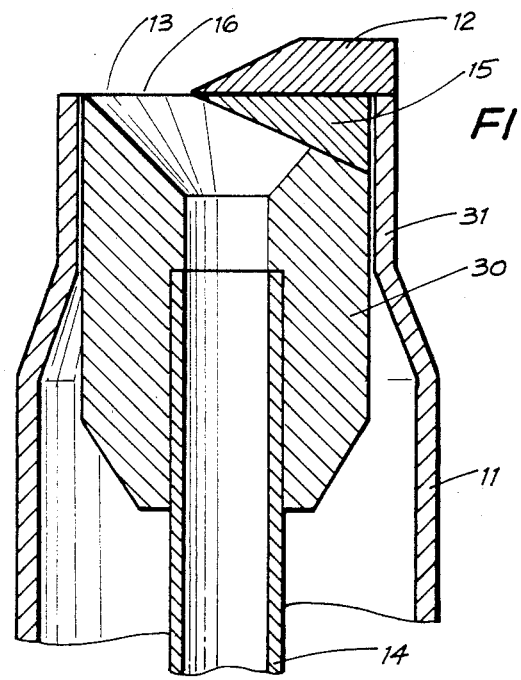
FIG. 3 is an enlarged longitudinal sectional view of the tip of the surgical instrument of FIG. 1 with the apertures in the end walls of the inner and outer tubes in register.
Figure 2:
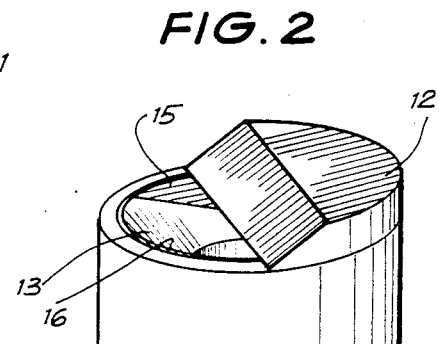
FIG. 2 is an enlarged perspective view of the tip of the surgical instrument of FIG. 1.
Figure 4:
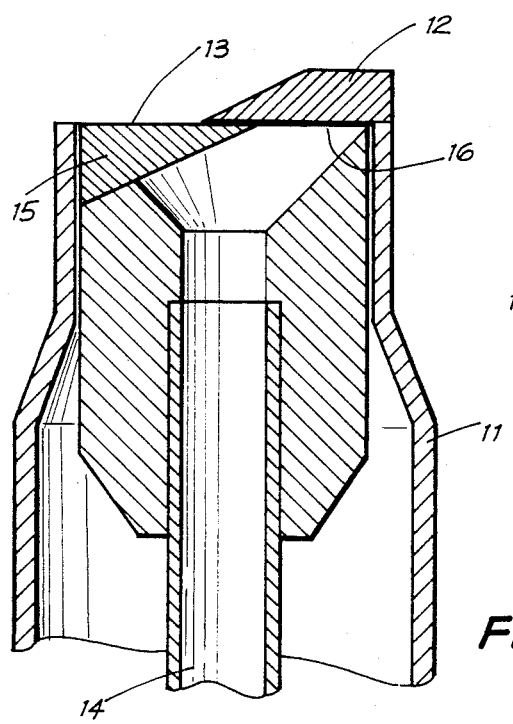
FIG. 4 is an enlarged longitudinal sectional view of the tip of the surgical instrument of FIG. 1 with the apertures in the end walls of the inner and outer walls out of register.

The surgical instrument 10 includes a first, outer tube 11 having at its free end an end wall 12 in which is provided an aperture 13 and a second, inner, tube 14 disposed within the outer tube 11 and rotatable relative thereto. An end wall 15 on the second tube 14 is provided with an aperture 16 which moves into and out of register with the aperture 13 in the outer tube 11 as the inner tube 14 is rotated. The inner tube 14 is mounted on a drive spindle 17 containing seals 18 to separate the spaces containing pressurised liquid from those forming the suction pathway, and is rotated in housing 26 about its longitudinal axis by motor means (not shown). An inlet port 19 is provided for introducing an irrigating liquid into the annular space 20 between the outer tube 11 and the inner tube 14 while an outlet port 21 is provided for the connection of the interior of the inner tube 14 with a suction source (not shown).

The outer tube 11 extends into a bore 27 in a cylindrical bush 22 and is held in angular register with the housing 26 by a radially extending pin 23 which engages in a slot in the end of the housing 26. The bush 22 is in turn positioned in a bore 25 of a housing 26, a radially directed flange 22A on the bush 22 bears against the free end of the housing 26 surrounding the end of the bore 25 and the bush 22 is held in place by a threaded collar 24 which engages witth a threaded outer surface of the housing 26. An "o" ring 28 is positioned in a circumferential groove 29 in the bush 22 to provide a liquid-tight seal between the bush 22 and the housing 26.

The inner tube 14 is at its cutting end provided with a collar 30 of increased diameter which just fits into a zone 31 of the outer tube 11 which is of reduced diameter. Adjacent its non-cutting end the inner tube 14 extends through, and is connected to a ferrule 32. At its end distal to the tip of the surgical instrument 10 the ferrule 32 is provided with a pair of diametrically opposed radially directed lugs 33 which extend into slots in one end of the drive spindle 17. A spring 34 extends between one end of the drive spindle 17 and a flange 35 at the end of the ferrule distal to the spindle 17. The spring 34 serves to push the ferrule 32, and the inner tube 14 attached thereto in a direction which forces the end wall 15 of the inner tube 14 into close juxtaposition with the end wall of the outer tube 11.

The end of the inner tube 14 adjacent the ferrule 32 extends into a bore 35 in the spindle 17 and is surrounded by an "o" ring to form a seal between the spindle 17 and the inner tube 14. The bore 35 communicates with a radial bore 36 which in turn communicates with an annular recess 37 which surrounds the spindle. The suction outlet port 21 in the housing 26 communicates with the annular recess 37.

The housing is formed on its side opposite the outlet port 21 with a radially extending bore 38 which opens into the annular recess 37 at one end and opens into an elongate slot 39 in the side wall of the housing 26 at the other. The slot 39 is so placed that a surgeon using the instrument can slide his thumb along the slot to control the amount of air flowing into the annular recess 37 through the slot 39 which in turn controls the amount of suction pressure which will be present in the inner tube 14.

The end walls 12 and 15 are provided along their edges bounding respectively the apertures 13 and 16 with a sharpened edge such that when the inner tube is rotated there will be a scissor like cutting action between those edges as the apertures are moving out of register.

In use the drive spindle 17 is connected to a motor of some suitable type such an an electric motor or a fluid turbine of the type used in dental drills, the inlet port 19 is connected to a source of isotonic saline solution or some other suitable irrigating liquid, and the outlet port 21 is connected to a source of suction pressure. Upon actuating the motor the inner tube will be rotated and as this happens the irrigating liquid will flow down the annular space 20 and between the collar 30 and the necked-down portion 30 of the outer tube 11. When the tip of the instrument 10 is placed in juxtaposition with tissue to be cut away and the slot 39 substantially closed the tissue is sucked into the inner tube 14 when the apertures 13 and 16 are in juxtaposition and the tissue so sucked into the tube is then cut off and drawn up the tube 14 as the tube 14 rotates.

I claim:

1. A surgical instrument comprising a first tube having at one end an end wall disposed in a plane substantially normal to the longitudinal axis of the first tube which end wall contains an aperture; a second tube disposed substantially coaxially within the first tube and having at one end an end wall disposed in a plane substantially normal to the longitudinal axis of the second tube which end wall is resiliently urged by resilient means into close juxtaposition with the end wall of the first tube; the end wall of said second tube containing an aperture; said apertures extending only in said end walls so that the side walls of said tubes are free of any apertures; means to enable the tubes to be rotated relative to one another about their common axis, the apertures in the end walls of the tubes each lying wholly within the plane of its associated end wall and the apertures being so placed in the end walls that they are moved into register and substantially completely out of register with one another as the tubes are rotated relative to one another; annular duct means defined between the first tube and the second tube discharging at said one ends of the tubes to direct a stream of a liquid to said one ends of the tubes; and duct means to connect the interior of the second tube to a source of suction, an edge portion of each aperture being sharpened such that the edge portions together form cooperating shearing blades as the apertures are moved out of register.

2. The surgical instrument as claimed in claim 1 in which the relative rotation of the tubes is achieved by holding the outer tube stationary and rotating the inner tube.

3. The surgical instrument as claimed in claim 1 in which the duct means to connect the interior of the second tube to a source of suction includes a by-pass path to admit air to said duct means.

4. The surgical instrument as claimed in claim 3 in which the by-pass comprises an aperture through a side wall of the surgical instrument which opens into said duct means, the effective cross sectional area of which aperture and by-pass being capable of manual adjustment.

* * * * *